United States Patent [19]
Molina

[11] Patent Number: 5,897,586
[45] Date of Patent: Apr. 27, 1999

[54] IMPLANTABLE DEFIBRILLATOR LEAD

[75] Inventor: J. Ernesto Molina, New Brighton, Minn.

[73] Assignee: Regents of The University of Minnesota, Minneapolis, Minn.

[21] Appl. No.: 08/911,236

[22] Filed: Aug. 15, 1997

[51] Int. Cl.$^6$ ..................................................... A61N 1/05
[52] U.S. Cl. ........................................... 607/129; 600/374
[58] Field of Search ........................... 607/122, 129–132; 600/373–375

[56] References Cited

U.S. PATENT DOCUMENTS

| | | |
|---|---|---|
| 4,938,231 | 7/1990 | Milijasevic et al. . |
| 4,998,975 | 3/1991 | Cohen et al. . |
| 5,052,407 | 10/1991 | Hauser et al. . |
| 5,109,842 | 5/1992 | Adinolfi . |
| 5,327,909 | 7/1994 | Kiser et al. . |
| 5,397,342 | 3/1995 | Heil, Jr. et al. . |
| 5,405,375 | 4/1995 | Ayers et al. ............................. 607/122 |
| 5,464,447 | 11/1995 | Fogarty et al. . |
| 5,476,503 | 12/1995 | Yang . |
| 5,482,037 | 1/1996 | Borghi .................................... 600/381 |
| 5,496,362 | 3/1996 | Kenknight et al. . |
| 5,542,173 | 8/1996 | Mar et al. . |
| 5,582,609 | 12/1996 | Swanson et al. ......................... 606/39 |
| 5,626,136 | 5/1997 | Webster, Jr. ............................. 600/373 |
| 5,673,695 | 10/1997 | McGee et al. .......................... 607/122 |

OTHER PUBLICATIONS

Lawton, et al., "Implantable Transvenous Cardioverter Defibrillator Leads: The Dark Side", *PACE*, vol. 19 (Sep. 1996), pp. 1273–1278.

*Lippincott's Illustrated Reviews: Pharmacology,*, R. A. Harvey, et al., Eds., "Antiarrhythmic Drugs", Ch. 17 (undated); pp. 161–170.

"Cardiac Defibrillators (Implantable External)", http://www.globind.com/310.htm, updated Feb. 12, 1997, pp. 1–2.

Abstract: (Embase No. 94378987) Luderitz, B., "Atrial fiibrillation and atrial flutter: Mechanisms and etiology (Vorhofflimmern und Vorhofflattern: Pathophysiologie und Pathogenese)", *Z. Kardiol.* (Germany), 1994, 83/Suppl. 5 (1–7). ISSN: 0300–5860.

Abstract: (Biosis No. 98001918) "Incidence, presentation, diagnosis, and management of malfunctioning implantable cardioverter–defibrillator rate–sensing leads", *Biological Abstracts* vol. 099, Iss. 001, Ref. 001918.

Abstract: (Biosis No. 98168022) "Implantable cardioverter–defibrillators and nonthoracotomy lead systems: Temporal stability of defibrillation energy requirements", *Biological Abstracts* vol. 099, Iss. 008, Ref. 108325.

Abstract: (Biosis No. 98045593) "Transvenous–subcutaneous implantation of the ICD", *Biological Abstracts* vol. 099, Iss. 003, Ref. 030137.

Abstract: (Biosis No. 97234818) Sensing–pacing lead complications with a newer generation implantable cardioverter–defibrillator: Worldwide experience from the Guardian ATP 4210 Clinical Trial:, *Biological Abstracts* vol. 097, Iss. 011, Ref. 151934.

Abstract: (Biosis No. 95128085) "Surgical experience with defibrillator implantation using nonthoracotomy leads".

Abstract: (Biosis No. 94116889) "Efficacy of automatic multimodal device therapy for ventricular tachyarrhythmias as delivered by a new implantable pacing cardioverter–defibrillator results of a European multicenter study of 102 implants".

Abstract: (Biosis No. 94036669) "A permanent transvenous lead system for an implantable pacemaker cardioverter–defibrillator nonthoracotomy approach to implantation".

Abstract: (Embase No. 96149786) "Performance of implantable defibrillator pacing/sensing lead adapters".

(List continued on next page.)

*Primary Examiner*—Jeffrey R. Jastrzab
*Attorney, Agent, or Firm*—Merchant, Gould, Smith, Edell, Welter & Schmidt, P.A.

[57] ABSTRACT

The invention includes an implantable epicardial defibrillator lead with a linear assembly of sensors and coils that is formed into a loop upon implanting in a patient and a method for implanting this lead on a diaphragmatic surface of the pericardium.

19 Claims, 5 Drawing Sheets

OTHER PUBLICATIONS

Abstract: (Embase No. 95184740) "Transvenous implantable cardiovascular defibrillator lead system: Experience in 28 patients".

Abstract: (Embase No. 95004885) "Implantation of an automatic defibrillator using a new nonthoracotomy approach".

Abstract: (Embase No. 94029687) "Sensing/pacing lead complications with a newer generation implantable cardioverter–defibrillator: Worldwide experience from the Guardian ATP 4210 clinical trial".

Abstract: (Embase No. 93209223) "Total pectoral implantation: A new technique for implantation of transvenous defibrillator lead systems and implantable cardioverter defibrillator".

Abstract: (Embase No. 93111895) "Surgical experience with defibrillator implantation using nonthoracotomy leads".

Abstract: Obadia, J.F., et al., "Nouvelle approche pour l'implantation des defibrillateurs automatiques utilisant la video–thoracoscopie [New approach for implantation of automatic defibrillators using videothoracoscopy]", *Ann. Cardiol. Angeiol.* (Paris, Sep. 1994), 43(7):384–388. (ISSN No. 0003–3928).

Abstract: Bocker, D., et al., "Comparison of frequency of aggravation of ventricular tachyarrhythmias after implantation of automatic defibrillators using epicardial versus nonthoracotomy lead systems", *Am. J. Cardiol.* (May 1, 1993), 71(12):1064–1068 (ISSN No. 0002–9149).

Abstract: Frumin, H., et al., "ICD implantation via thoracoscopy without the need for sternotomy or thoracotomy", *Pacing Clin. Electrophysiol.* (Feb. 1993), 16(2):257–260 (ISSN No. 0147–8389).

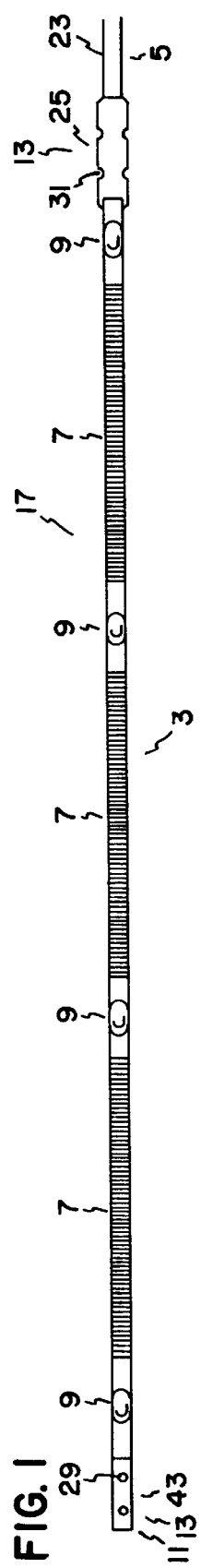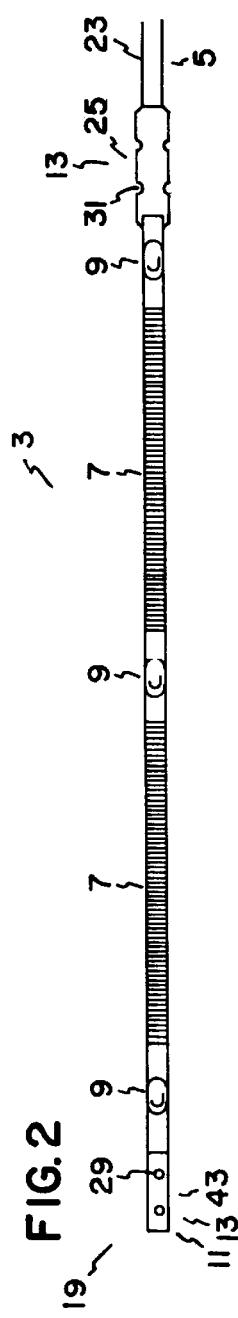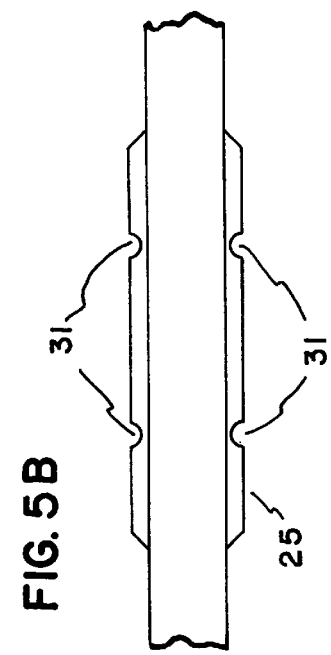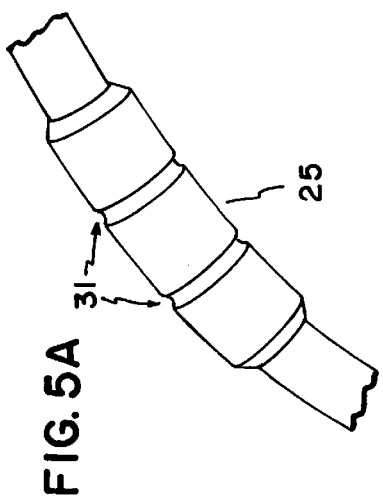

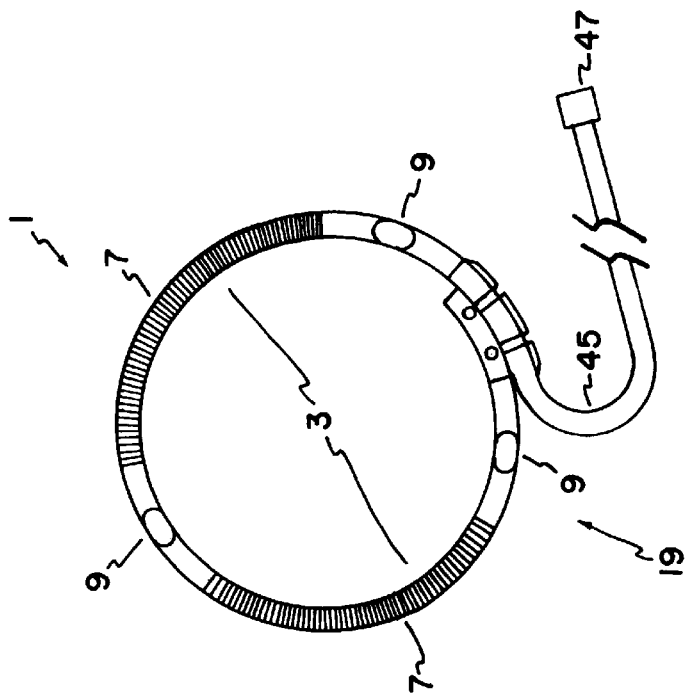
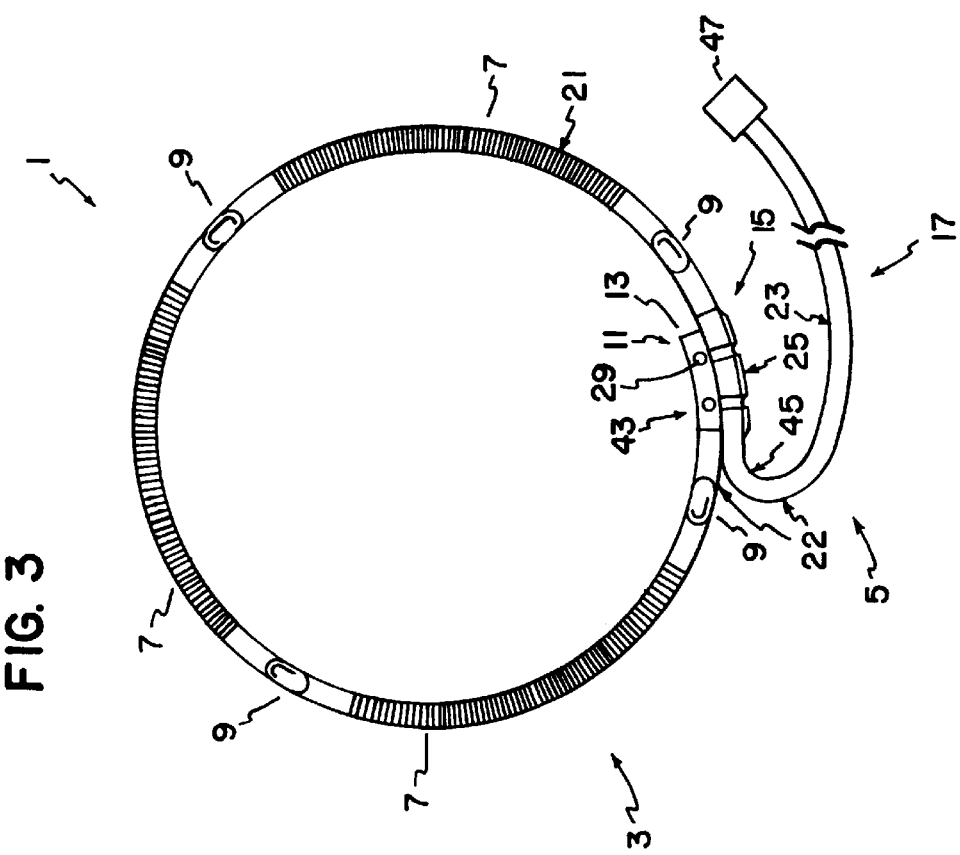

FIG. 7A
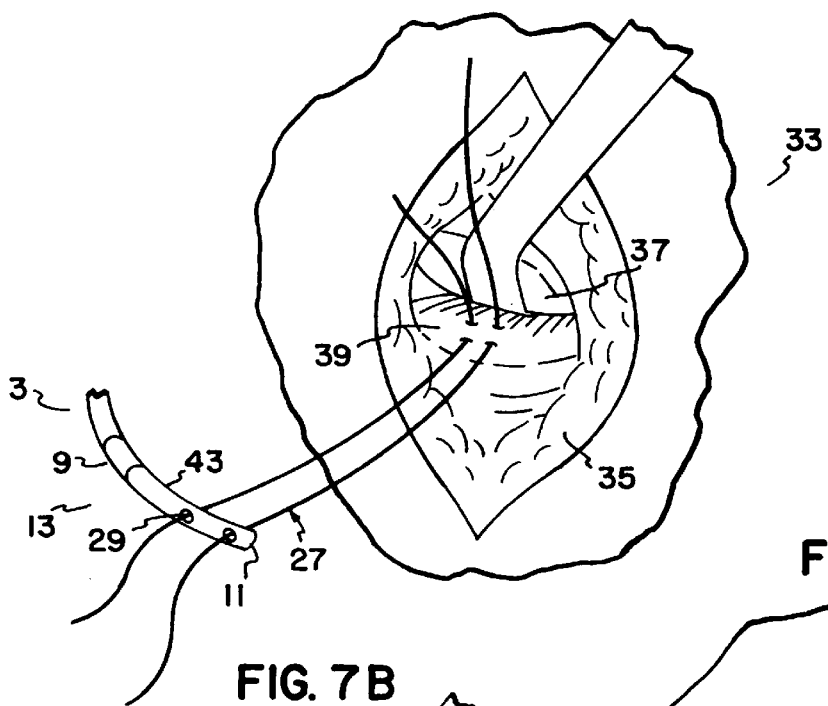
FIG. 7B
FIG. 7C
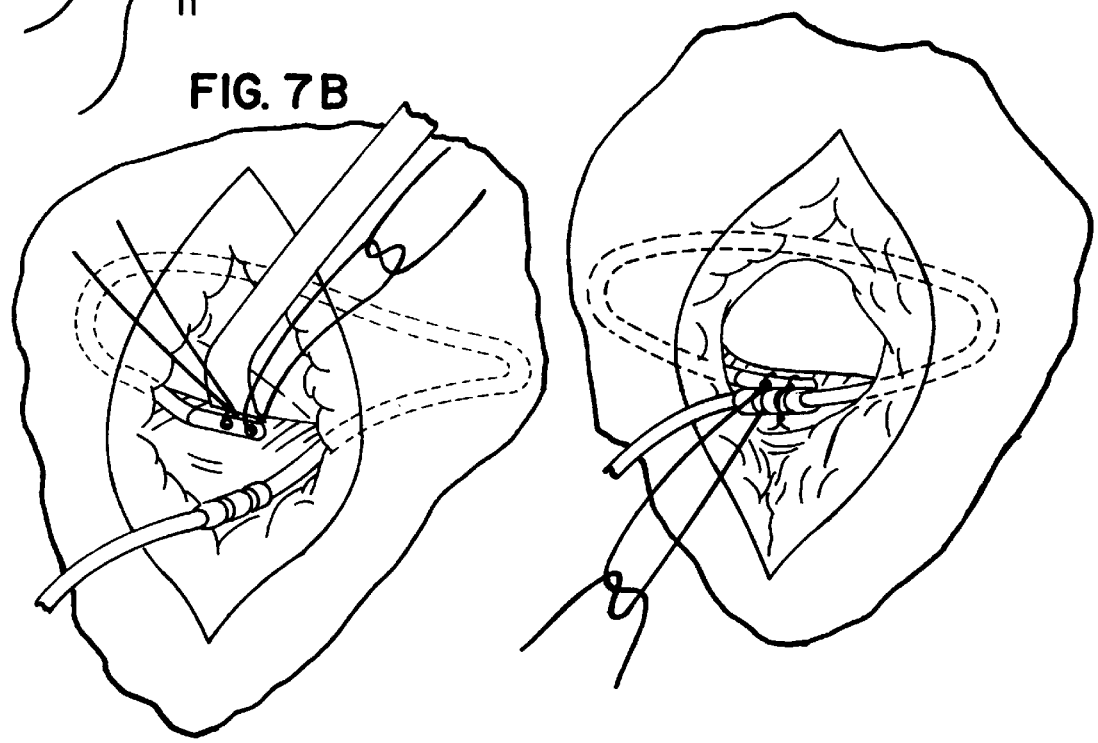

IMPLANTABLE DEFIBRILLATOR LEAD

BACKGROUND OF THE INVENTION

Implantable cardiac defibrillators include patch defibrillators with a lead configured as a patch, which is attached to the surface of the heart or embedded in the patient subcutaneously. For example, one early patch lead included a rectangular patch that is applied around the patient's heart and is implanted by performing a thoracotomy on the patient. Other modifications or additions to the early patch designs were aimed at improved performance, improved patient tolerability, and simplified implanting. Despite improvements, patch leads typically suffer from a significant degree of crinkling, migration, erosion, and other problems related to the patch. Another drawback to patch leads is the need for surgery to implant the patch lead. This results in significant levels of operative mortality and infection of the patch, which can cause a life-threatening condition. Patch leads are undesirable because of these structural problems and risk of fatal complications.

Transvenous implanting of defibrillator leads was developed as an alternative to patch defibrillators. A transvenous lead including a defibrillator coil is typically inserted via the subclavian, internal jugular, or cephalic veins. Compared to the patch defibrillator leads, the transvenous leads show a reduction of operative mortality and are easier to implant. However, many transvenous systems require several coils in the right ventricle, the superior vena cava, the innominate vein, and sometimes even in the coronary sinus. This requires numerous leads all going in the same vein. This is undesirable because of consequences such as fibrosis or occlusion of the subclavian vein, obliteration of the superior vena cava, or simply mechanical obstruction of the vein. In addition, some of the transvenous systems require placement of a patch on the chest wall to render them effective. Using a patch results in all of the potential problems of patch leads and removes many of the advantages of the transvenous lead.

Although using transvenous leads reduced mortality and the number of complications, compared to patch leads, significant problems still occurred. One major problem is that transvenous leads migrate within the patient. Removal of a transvenous lead can also be a severe problem. Some of patients receiving transvenous leads are transplant candidates who receive a transvenous defibrillator system as a temporary measure, while awaiting transplant, to prevent sudden death from arrhythmia. In this case removal may not be a problem if the lead is removed soon after implantation. However, most of the transvenous leads having been in place for several weeks or months are extremely difficult to remove to allow the implant of the donor heart.

Because an intravenous lead that has been implanted for a long time is extremely difficult to remove, they can create problems if they fail. For example, there may not be room in the vein for additional leads. Overall, removing a transvenous lead requires a risky and difficult operative procedure. Frequently, removal requires cardiopulmonary bypass.

Transvenous defibrillator leads also cause other significant complications. For example, a transvenous lead can result in thrombosis of the subclavian or innominate veins, a complication which is usually irreversible. Severe fibrosis of the leads on the endocardial surface of the heart also occurs. This increases the defibrillation thresholds and makes removal of the leads impossible. Other complications include dislodgement, right ventricular perforation, creation of ventricular septal defect, infection, right atrial thrombus formation, subclavian vein thrombosis, pulmonary embolism, insulation breakage, development of a crush or compression fracture of the leads, and embolization of the distal lead.

Problems related to the use of transvenous leads increase health care costs. Complications of transvenous leads result in hospital readmissions, operative lead revisions, lead replacement, and lead failures. The so-called lead crush syndrome, which is the pinching of the transvenous leads at the thoracic inlet between the clavicle and the first rib is a very well known problem, not only with defibrillators, but pacemaker systems as well. The problem of chronic subclavian vein obstruction is not a mild one and some of those patients cannot be treated, even surgically, to reestablish the patency of the vessels.

Many patients are not candidates for receiving a transvenous defibrillator. For example, patients who have had either previous transvenous systems and have developed fibrosis and/or occlusion of the subclavian vein are not candidates for further transvenous leads. Some patients develop obliteration of the superior vena cava due to multiple leads previously placed. Some patients with transvenous pacemakers of the bipolar type, which include two leads in addition to the lead used for the defibrillator, do not have room for additional leads. The innominate, subclavian, and superior vena cava veins do not have limitless capacity to take so much hardware. Other patients, such as children, simply are not candidates for transvenous defibrillator systems. Although not a large population, there are children who require defibrillator therapy and are unable to receive it because of a lack of a proper device, either of the transvenous or patch designs.

To overcome these limitations and avoid these problems, a new simple epicardial implantable defibrillator lead was developed.

SUMMARY OF THE INVENTION

The present invention relates to a defibrillator lead, and a method of implanting the lead that meet the needs described above. The defibrillator lead of the invention includes an system of one or more coils and one or more sensors in a linear arrangement and which can be configured as a loop. The lead also includes a conductor system for coupling the loop system to a pulse generator. The lead can be configured for use in an adult or a child. Compared to a pediatric lead, an adult lead has one or more additional coils, one or more additional sensors, a larger diameter loop, or a longer connector system. In one preferred embodiment, the lead is configured for connection to and used for defibrillating with standard pulse generators and pulsing protocols.

The lead can be implanted in a patient by a method that does not require opening either the chest or the heart. The lead can be introduced into the pericardium through a transxiphoid or subxiphoid incision and secured to the diaphragmatic surface of the pericardium. In a preferred embodiment, the lead is fastened in a looped configuration and secured to the pericardium with a single suture. The lead can be configured and implanted to be removable.

BRIEF DESCRIPTION OF THE DRAWINGS
Brief Description of the Drawings

FIG. 1 shows a configuration of the epicardial implantable defibrillator lead suitable for implanting in an adult. The loop system is in a linear arrangement which can be implanted in an adult patient and formed into a loop during implanting. The connector system is truncated in the Figure.

FIG. 2 shows a configuration of the epicardial implantable defibrillator lead suitable for implanting in a child, a pediatric lead. The loop system is in a linear arrangement which can be implanted in a pediatric patient and formed into a loop during implanting. The connector system is truncated in the Figure.

FIG. 3 shows a configuration of the adult epicardial implantable defibrillator lead with the loop system formed into a loop and showing the ends of the connector system. This lead corresponds to the adult lead shown in FIG. 1.

FIG. 4 shows a configuration of the pediatric epicardial implantable defibrillator lead with the loop system formed into a loop and showing the ends of the connector system. This lead corresponds to the pediatric lead shown in FIG. 2.

FIG. 5 shows a sleeve portion from one embodiment of a closure segment.

FIGS. 7A, 7B and 7C show a schematic presentation of the process of implanting the epicardial implantable defibrillator lead.

DETAILED DESCRIPTION OF THE INVENTION

The Epicardial Implantable Defibrillator Lead

The lead of the invention is now discussed with reference to particular embodiments shown in FIGS. 1–9.

The epicardial implantable defibrillator lead of the invention includes a loop system with a linear array of one or more coils and one or more sensors, which can be arranged as a loop. The lead of the invention also includes a connector system adapted and configured to couple the loop system to a pulse generator. The connector system includes a conductor within an insulating sheath or cover.

Within the loop system, one or more coils and one or more sensors are arranged in a linear array. The linear array provides for ease of implanting the lead in a patient, facilitates removal from the patient, and an advantageous arrangement of one or more coils and one or more sensors. One advantageous aspect of this arrangement of coils and sensors is that only a single component need be implanted in a patient to provide both sensors and coils. Another advantageous aspect of this linear array of sensors and coils is that the spatial relationship of the coils and sensors in the linear array provides a predetermined arrangement of coils and sensors when the lead is inserted into a patient and formed into a loop.

A coil includes a conductive portion that is typically a coiled conductor and can form all or part of the coil. The coil is adapted and configured to couple to a sensor. By coupled it is meant that a coil and sensor are physically joined by any number of ways understood by those practicing the invention including physically connected, fused, cemented, welded, or the like. Sensor and coil are electrically isolated or insulated from one another. One or more coils and one or more sensors can also be formed as a one piece arrangement. One sensor to be employed in the lead of the invention is the type used in defibrillators or pacers for sensing heart rhythm and providing data regarding the rhythm to a pulse generator. The lead of the invention also includes a closure segment adapted and configured to form a loop from the arrangement of sensors and coils within the insulating sheath. The lead of the invention can also include an attachment system adapted and configured for attaching the lead to a patient.

The lead of the invention can be adapted and configured for implanting in an adult or a child. Adults are larger than children, and they typically require a larger loop so that the pulse goes through the entire heart and a longer connector system capable of reaching the pulse generator. Reflecting this difference in size, a pediatric lead of the invention typically includes two coils and three sensors and an adult lead typically includes three coils and four sensors.

Figure 8:
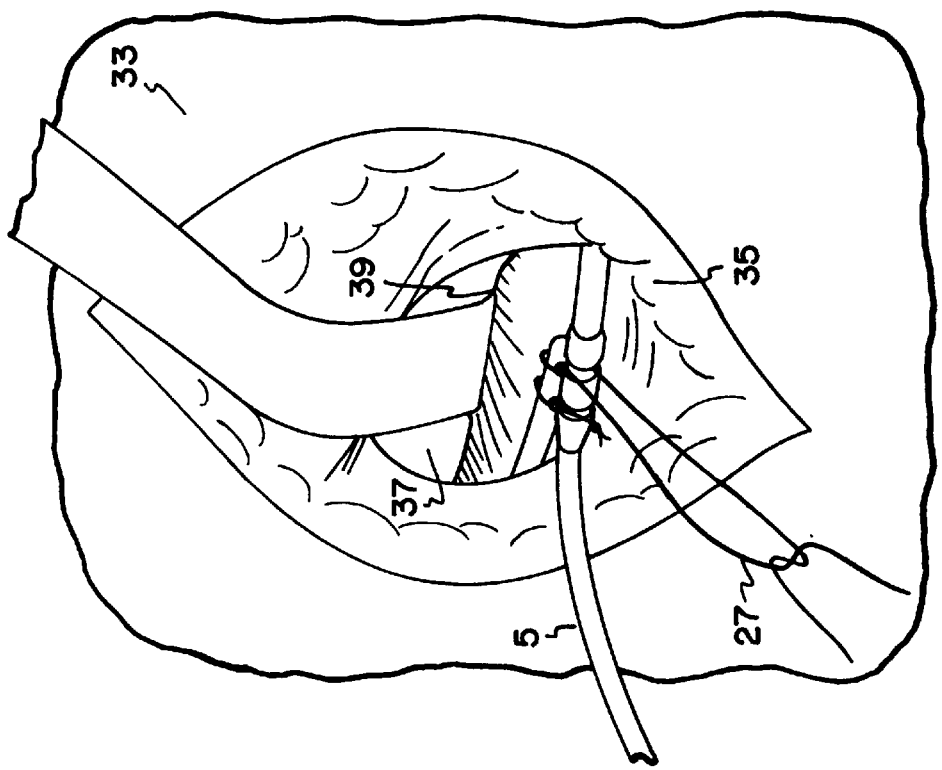
FIG. 8 illustrates a single point of attachment for the loop portion of the lead.
Figure 6:
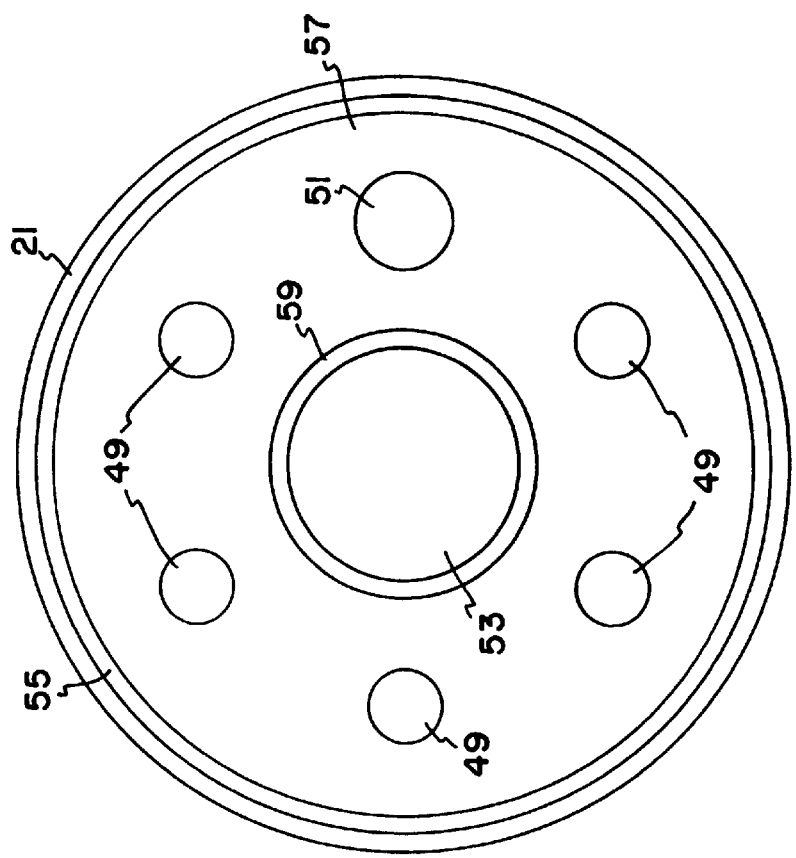
FIG. 6 shows a cross sectional view of an embodiment of the loop system including a conductive portion of a coil, several conductor members, a memory member, and a stylet.
Figure 9:
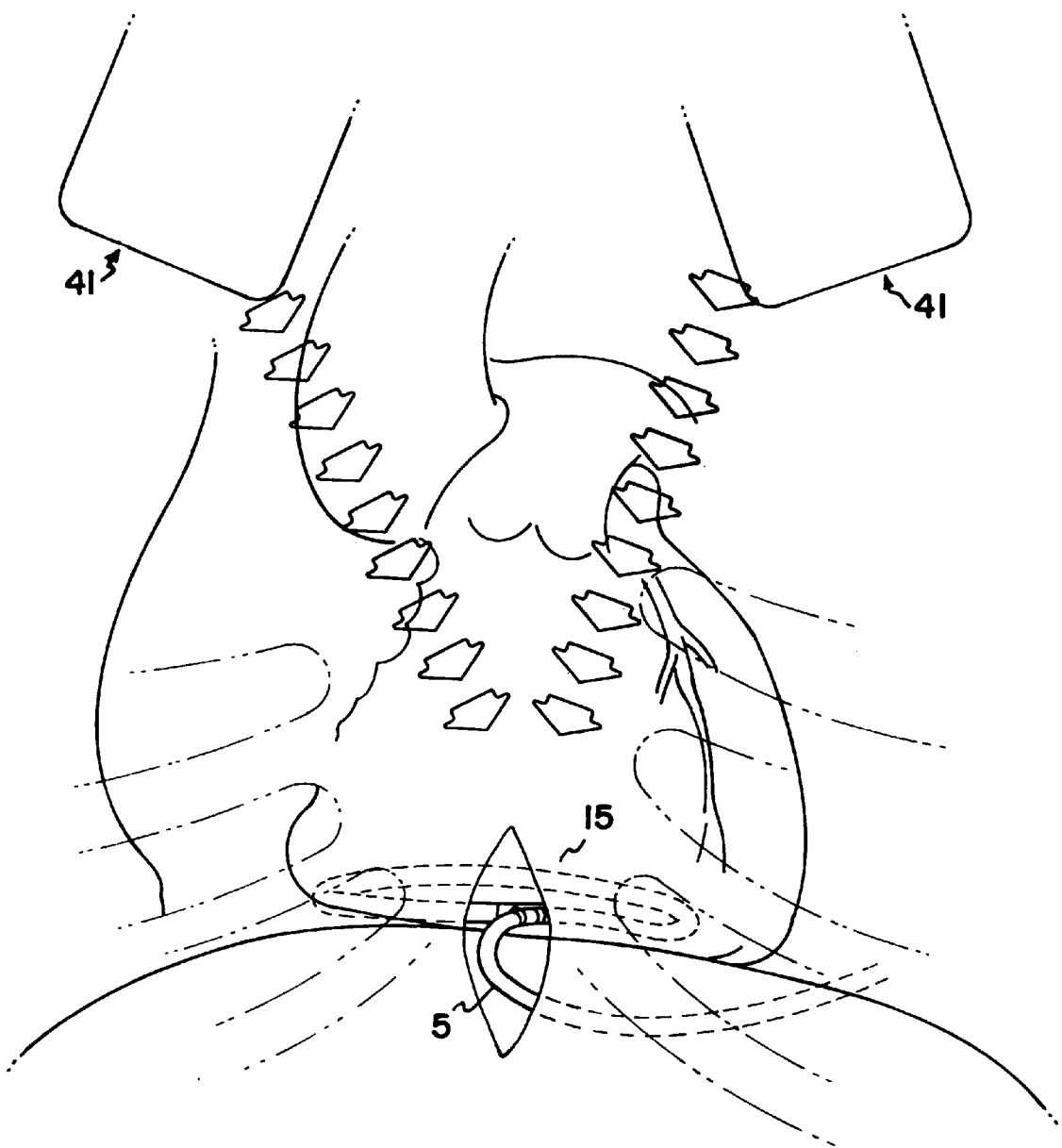
FIG. 9 is a schematic illustration of the direction of the vectors of electrical energy traveling between the pulse generator and the epicardial implantable defibrillator lead.

FIGS. 1–4 show preferred embodiments of lead 1. As described later herein FIGS. 1 and 3 show an adult lead 17 and FIGS. 2 and 4 show a pediatric lead 19. Each lead 1 shown in FIGS. 1–4 has a loop system 3 and a connector system 5. As shown, loop system 3 has a linear arrangement of coils 7 and sensors 9 that can be formed into a loop. In these Figures, loop system 3 has alternating sensors 9 and coils 7, with the loop 15 beginning and ending with a sensor 9. Each sensor 9 is coupled, but not electrically connected, to at least one coil 7, and each coil 7 is coupled to two sensors 9. Coils and sensors are coupled using standard connectors used for coupling components of defibrillators and which insulate sensor 9 from coil 7 as they connect to the pulse generator. Internally, as shown in FIG. 6, loop system 3 can include one or more insulated conductive members 49, each of which connect one or more individual sensors 9 or one or more individual coils 7 to connector system 5. Another internal component of loop system 3 can be biasing or memory member 51, which provides biasing force that urges loop system 3 to form loop 15 within a body. Loop system 3 an be generally tubular and define lumen 59 that provides access for inserting stylet 53. Stylet 53 aids in insertion of loop system 3 into a patient, and can provide additional stiffness as loop 15 is formed in the patient.

Connector system 5 connects loop system 3 to a pulse generator 41. As shown in FIGS. 3 and 4, connector system 5 has ends 47 and 45 for coupling to pulse generator 41 and to loop system 3, respectively. A standard connector can be used for coupling to pulse generator 41 and to loop system 3.

To form a loop 15 from loop system 3 and to join loop system 3 to connector system 5, a closure segment 13 is provided. As shown in FIGS. 3 and 4, ends of loop system 3 are joined by closure segment 13 to form loop 15. Closure segment 13 includes sleeve 25 (shown in FIGS. 1–5) and perforation member 43 (shown in FIGS. 1–4), which are adapted and configured for closing the loop with a suture. Preferably, perforation member 13 has perforations 29 through which suture 27 can be threaded. Preferably, sleeve 25 has in its surface grooves 31, which are configured to restrain suture 27. The length of loop system 3 between perforation member 13 and sleeve 25 is the circumference of loop 15. Other closure systems for closing the loop and forming the loop/connector lead can be employed, such as using additional sutures or stitches as desired to obtain stability of the lead relative to the pericardial surface.

Generally, loop 15 can be formed in any of a variety of ways. Loop system 3 can be formed into a loop 15, for example, by attaching an end 11 of loop system 3 to a portion of either loop system 3, connector system 5, or closure segment 13. Alternatively, a portion of loop system 3 can be attached to a distal portion of loop portion 3, or to connector system 5, or closure segment 13. In another embodiment, loop 15 can be formed using closure segment 13, which can employ any of a variety of mechanisms for forming a loop 15 from loop system 3. For example, loop 15 can be closed by an apparatus or system that snappably engages, welds, adheres, or otherwise fastens a portion of loop system 3, preferably end 11, to loop system 3, closure segment 13, or connector system 5.

In FIGS. 1–4, each coil 7 is coupled to two sensors 9, and each sensor 9 is coupled to one or more coils 7. Generally, each coil 7 can couple either to another coil 7 or a sensor 9, and each sensor 9 can couple to another sensor 9 or coil 7. Thus, the lead of the invention can be configured in a variety of arrangements. In addition, a sensor 9 or a coil 7 can be configured to couple with, or can include components of closure segment 13. For example, a coil 7 or sensor 9 can include features analogous to grooves 31 of sleeve 25 or to perforations 29 of perforation member 43.

As shown in FIGS. 1–4, coil 7 is made from materials and in configurations known in the art for high current, low resistance defibrillator coils. In FIGS. 1–4 entire coil 7 is shown as a conductor, although one of skill in the art will appreciate that only a portion of coil 7 need be of conductive material or a discrete conductor element can be included as a portion of the coil. For example, coil 7 can be a single or multifilar coil, a tinsel wire coil, a braided coil, or the like. Typically, coil 7 is made from a material such as MPN30, Eljalloy, nitinol wire, titanium wire coated with platinum, a nickel-titanium alloy, platinum-iridium, a similar metal conductor, or the like. Typically, the conductive portion 21 of coil 7 is shaped as a generally tubular coil, helix or spiral, is exposed over all of or a majority of the length of coil 7, and is insulated from any sensor 9. Typically, each coil 7 is spatially isolated from and is insulated from any other coil 7. The generally tubular conductive portion 21 of coil 7 can include in its lumen 55 a conductor member 49 enclosed within an insulator 57 (as shown in FIG. 6), for purposes such as connecting connector system 5 to sensor 9 or to another coil 7. Lumen 55 can also house memory member 51, stylet 53, or the like (FIG. 6).

A sensor 9, shown in FIGS. 1–4, can be made from materials and in configurations known in the art for sensors for defibrillators or pacers. For example, sensor 9 can be a sense electrode, a surface electrode for sensing and pacing with or without steroid eluting construction, or the like. Sensor 9 is typically of the same diameter of loop system 3 and coil 7, or slightly prominent. If sensor 9 is prominent it will typically be tapered at both ends to facilitate removal of the lead from the patient, if this becomes necessary. Typically, a sensor 9 can detect a cardiac rhythm and pace the ventricles without penetrating the epicardium. Sensor 9 can be coupled to pulse generator 41 either individually, so that pulse generator 41 can receive a signal from sensor 9 alone, or jointly with one or more additional sensors 9. Typically, each sensor 9 is connected individually to an insulated conductor member 49 that extends to connector system 5. Sensor 9 can include in its lumen 55 a conductor member 49 enclosed within an insulator 57 (as shown in FIG. 6), for purposes such as connecting connector system 5 to another sensor 9 or to coil 7. Lumen 55 can also house memory member 51, stylet 53, or the like (FIG. 6). The lead can also be provided with one sensor or pacer implanted in the myocardium.

As shown in FIGS. 3 and 4, connector system 5 is enclosed in insulating sheath 23. Connector system 5 can be made from materials and in configurations known in the art for connecting a high current, low resistance defibrillator lead to a pulse generator 41. Typical connector system configurations for connecting to a pulse generator are known as universal pin connectors. Typically, connector system 5 includes a conductor made from a material such as MPN30, Elj alloy, a similar metal material, a low resistance composite material, such as drawn braised stranded or drawn filled tubes, or the like. Connector system 5 is typically configured as an elongated conductor that can be enclosed in a tubular insulating cover 23, and coupled to loop system 3 and pulse generator 41.

Insulating sheath or cover 23 is typically a generally tubular sheath that encloses generally tubular connector system 5. Second insulating sheath 23, like other insulating materials used in the lead of the invention, is made of a material suitable for insulating electrical components from the human body and for implanting in the human body, such as silastic or another silicone containing rubber or polymer material. However, insulating sheath 23 can be of a material or in a configuration suitable for enclosing connector system 5.

Lead 1, loop system 3, and connector system 5 can be configured to form an adult lead 17 or a pediatric lead 19, as shown in exemplary embodiments in FIGS. 1–4. An adult lead 17, compared to a pediatric lead 19, typically is longer and includes more coils 7 and sensors 9. The adult body and heart are typically larger than a child's, which can require a larger lead 1.

Adult Epicardial Implantable Defibrillator Lead

A typical adult lead 17, shown in FIGS. 1 and 3, includes three coils 7, four sensors 9, and a connector system 5 constructed to connect to a pulse generator 41 implanted above the heart in an adult chest. A preferred adult lead 17 includes a plurality of sensors 9, typically about two to about six sensors 9, preferably about four sensors 9 (FIGS. 1 and 3), that act as a sensing point to detect cardiac function and also for pacing of the heart, if needed. Typically, each sensor 9 is about 1–3 cm in length, preferably about 2 cm. A preferred adult lead 17 includes a one or more coils 7, typically about one to about five coils 7, preferably about three coils 7 (FIGS. 1 and 3), that provide defibrillation current. Typically, each coil 7 is about 4–6 cm in length, preferably about 5 cm. As shown in FIGS. 1 and 3, the coils and sensors of an adult epicardial defibrillator lead of the invention are generally cylindrical or tubular in shape with an outside diameter of about 2–4 mm, preferably about 3 mm.

A typical adult lead 17 shown in FIGS. 1 and 3 measures, from end 47 of connector system 5, which connects to a pulse generator 41, to end 11 of loop system 3, about 55–70 cm, preferably about 62.5 cm. In such an adult lead 17, loop system 3 is typically about 20–25 cm long, preferably about 22.5 cm, which forms a loop preferably about 7.5 cm in diameter. Connector system 5 of adult lead 17 is typically about 30–50 cm long, preferably about 40 cm. The length is chosen to allow sufficient distance to connect to pulse generator 41, which is advantageously placed in the upper chest at the subclavicular area.

Pediatric Epicardial Implantable Defibrillator Lead

A typical pediatric lead 19, shown in FIGS. 2 and 4, includes two coils 7, three sensors 9, and a connector system 5 constructed to connect to a pulse generator 41 implanted above the heart in a child's chest. A preferred pediatric lead 19 includes a plurality of sensors 9, typically about one to about five sensors 9, preferably about three sensors 9 (FIGS. 2 and 4), that act as a sensing point to detect cardiac function and also for pacing of the heart, if needed. Typically, each sensor 9 is about 1–3 cm in length, preferably about 2 cm. A preferred pediatric lead 19 includes one or more coils 7, typically about one to about three coils 7, preferably about two coils 7 (FIGS. 2 and 4), that provide defibrillation current. Typically, each coil 7 is about 4–6 cm in length, preferably about 5 cm. As shown in FIGS. 2 and 4, the coils and sensors of a pediatric epicardial defibrillator lead of the invention are generally cylindrical or tubular in shape with an outside diameter of about 2–4 mm, preferably about 3 mm.

A typical pediatric lead 19 shown in FIGS. 2 and 4 measures, from end 47 of connector system 5, which connects to a pulse generator 41, to end 11 of loop system 3, about 25–55 cm, preferably about 40 cm. In such an pediatric lead 19, loop system 3 is typically about 10–20 cm long, preferably about 15 cm, which forms a loop preferably about 5 cm in diameter. Connector system 5 of pediatric lead 19 is typically about 15–35 cm long, preferably about 25 cm. The length is chosen to allow sufficient distance to connect to pulse generator 41, which is advantageously placed in the upper chest at the subclavicular area.

Implanting the Epicardial Implantable Defibrillator Lead

The lead of the invention is advantageously positioned as a loop between the inferior surface of the heart and the dome of the diaphragm. The loop can be created by tying or stitching together a tip of the lead to an axis behind the last coil. The loop includes the active end of the lead coiled upon itself as a loop. One configuration of the lead allows the linear lead to be introduced through a small subxiphoid incision, the loop being formed during introduction, the loop structure being closed by a suture that also fastens the lead to the patient.

Implanting the lead of the invention is illustrated schematically in FIGS. 7A, 7B and 7C. Lead 1 can be implanted in patient 33 by a method including making a transxiphoid or subxiphoid incision 35 in patient 33. Using such a simple approach, lead 1 typically is implanted without use of fluoroscopy, but is done under direct vision in the operating room. Incision 35 allows access to pericardium 37 and to a diaphragmatic surface 39 of pericardium 37. Lead 1 can be inserted into pericardium 37 through incision 35. Such an incision 35 opens pericardium 37 and only a small incision 35 opening on a small space is needed to place stitches 27 on diaphragmatic surface 39 of pericardium 37.

Advantageously, lead 1 is secured to diaphragmatic surface 39 of pericardium 37, for example using sutures 27 and end 11, before advancing the remainder of lead 1 into pericardium 37. When an appropriate amount of lead 1 has been advanced into pericardium 37 loop 15 can be closed, for example with suture 27, end 11, and sleeve 25. Perforation member 43 at end 11 of loop system 3 can include a perforation 29, preferably two perforations 29, through which one or more stitches 27 can be placed. Stitch 27 is used to anchor end 11 to the dome of the diaphragm 39 at the xiphoid level and to close loop 15. Alternatively, loop 15 can be closed prior to advancing lead 1 or loop system 3 into pericardium 37. Before or after the loop is secured, stylet 53 can be removed from loop system 3. Once secured, loop 15 advantageously has a horizontal position over the diaphragmatic surface of the pericardium (as shown in FIGS. 7A, 7B, 7C and 9) and lays over the dome of diaphragm 39 between diaphragm 39 and the inferior surface of the heart. Advantageously, lead 1 is anchored to diaphragm 39 only at the point where tip 11 and sleeve 25 are tied together.

After lead 1 is secured to diaphragmatic surface 39 of pericardium 37 of subject 33, incision 35 can be closed and connector system 5 can be coupled to pulse generator 41. For connection to pulse generator 41, connector system 5 is tunneled up to the subclavicular area where pulse generator 41 is implanted, usually on the left side of patient 33, but the right side can be used as well. Advantageously, lead 1 lays horizontally covering the entire inferior surface of the heart and pulse generator 41 can be located on the left or right of the upper chest. Preferably pulse generator 41 is positioned in the subclavicular area, preferably retropectorally.

Because the entire ventricular septum in the human has a generally horizontal orientation where the right ventricle lies on top behind the sternum and the left ventricle is posterior to it and towards the left, any electrical shock coming from the upper part of the body (subclavicular right or left) to reach loop lead 1 will typically have a vector generally shaped like a cone or a pyramid and the current will have to go through the entire thickness of the ventricle including the septum. Vectors of current obtained using the lead of the invention are shown schematically in FIGS. 7A, 7B and 7C. The area covered by the lead of the invention, therefore, will be substantially more than a single straight lead placed inside the right ventricular chamber as it occurs with a transvenous lead system. No additional intravenous lead or patch lead is required to supplement the loop lead of the invention. Advantageously, in a lead with multiple sensors, at least one sensor maintains contact with the heart at all times.

Testing involved with this lead is advantageously reduced compared to conventional intravenous leads or patch leads, since the lead of the invention is one lead placed in the pericardium. Advantageously, even in patients who have undergone previous cardiac surgery, there won't be any need to reopen the entire chest. Through the subxiphoid approach, the inferior surface of the heart could be dissected to a significant distance to position a lead of the invention. In cardiac surgery patients who have had previous interventions, the only surface that remains relatively free of adhesions or easy to enter is the inferior surface of the heart which is the space between this and the dome of the diaphragm, which is the area where the lead of the invention is implanted. This type of lead can also be implanted in children through a small incision in the subxiphoid area.

Method of Treatment Using the Epicardial Implantable Defibrillator Lead

The lead of the invention can be used to treat disorders requiring defibrillation by a method including determining that a patient needs defibrillation, implanting a defibrillator lead of the invention, sensing an arrhythmia, and activating the defibrillator lead to provide defibrillation. Another method for treating arrhythmia in a patient in which the lead has already been implanted includes sensing an arrhythmia and activating the defibrillator lead to provide defibrillation. The lead of the invention can be activated by pulse generator systems known in the art.

The disorder requiring defibrillation can be diagnosed and detected by methods known in the art. Disorders requiring defibrillation include an arrhythmia arising from alteration in impulse generation leading to enhanced or abnormal automaticity, or from an abnormality in impulse conduction, which can result in the reentry phenomenon; an atrial arrhythmia such as atrial flutter or fibrillation, and paroxysmal supraventricular tachycardia; a ventricular arrhythmia such as acute ventricular tachycardia, or a refractory ventricular arrhythmia or tachycardia; a supraventricular arrhythmia or ectopic arrhythmia; an arrhythmia arising during or associated with myocardial ischemia or myocardial infarction; and an arrhythmia leading to sudden arrhythmic death.

Removing the Epicardial Implantable Defibrillator Lead

Advantageously, if the lead is no longer needed or if complications arise, the lead can be removed by cutting the stitch holding it to the pericardium and sliding the lead out, for example, by pulling on the connector system. This can be done under local anesthesia. Such simple removal is in contrast to the major dissection or surgical procedure involving exposure of the heart, which is required to remove an intravenous lead or an epicardial patch that has become infected or has eroded into the myocardium.

Indications for the Use of the Epicardial Implantable Defibrillator Lead

The epicardial implantable defibrillator lead of the invention can be the first-line approach for any patient who needs a defibrillator. However there are numerous indications for which the lead of the invention is particularly advantageous. For example:

1. When a single transvenous lead placed in the right ventricle is not effective, or requires additional electrodes to function adequately, the lead of the invention is advantageous compared to implanting additional electrodes to compensate for ineffectiveness of the single transvenous lead.
2. When a transvenous system fails, or is no longer effective, it can be replaced by a lead of the invention.
3. The lead of the invention is advantageous for all candidates for heart transplant who have a need for an implanted defibrillator lead while awaiting transplantation. Transvenous leads cause serious problems in a heart that is to be excised.
4. When a transvenous lead system cannot be implanted due to upper vein occlusions, the lead of the invention can be implanted.
5. In children or small patients who cannot accept transvenous leads due to the small size of their veins.

The present invention may be better understood with reference to the following example. The example is intended to be representative of specific embodiments of the invention, and are not intended as limiting the scope of the invention.

EXAMPLE

Leads of the invention have been implanted in lambs. Each lead implanted in a lamb had 2 coils, 1 sensor, a loop system 22 cm long, and a connector system 45 cm long. The lambs were tested for thresholds in the acute stage at 3 months and 9 months after implanting the lead of the invention. The lambs were also subjected to 2 periodic CT scans or chest X-rays to assess whether the lead had become either displaced or dislodged.

None of the leads were displaced or dislodged. In each of the lambs, cardiac electrical parameters remained satisfactory up to 9 months following the implant. After 10 months the lambs remain in good health and the lambs have been defibrillated after inducing ventricular fibrillation in every case.

The invention has been described with reference to various specific and preferred embodiments and techniques. Since many embodiments of the invention can be made without departing from the spirit and scope of the invention, the invention resides in the claims hereinafter appended.

I claim:

1. An epicardial implantable defibrillator lead comprising:
   a loop system having a first end and a second end, the loop system comprising a sensor, a coil, and a closure segment comprising a perforation member and a sleeve; the coil comprising a generally tubular conductive portion defining a lumen, the lumen comprising an insulator, the insulator enclosing a conductor member, a memory member, or both; the sensor, coil, perforation member and sleeve being coupled in linear arrangement with the perforation member located proximal to the first end and the sleeve located proximal to the second end; and
   a connector system having a first end and a second end, the first end of the connector system coupled to the second end of the loop system, the second end adapted to be coupled to a pulse generator, the connector system comprising an insulating cover enclosing a conductor; the conductor passing through the connector system and connecting with either the coil or sensor.

2. The defibrillator lead of claim 1, wherein the lead is a pediatric lead.
3. The defibrillator lead of claim 2, wherein the loop system comprises three sensors and two coils, each coil being coupled to two sensors.
4. The defibrillator lead of claim 1, wherein the lead is an adult lead.
5. The defibrillator lead of claim 4, wherein the loop system comprises four sensors and three coils, each coil being coupled to two sensors.
6. The defibrillator lead of claim 1, wherein the sensor detects cardiac rhythm and paces a ventricle without penetrating the epicardium.
7. The defibrillator lead of claim 1, wherein the insulating cover comprises silicon or silastic.
8. The defibrillator lead of claim 1, wherein the perforation member and the sleeve, when connected retain the loop system as a loop.
9. The defibrillator lead of claim 8, wherein the perforation member comprises perforations therein for threading a suture therethrough and the lead further comprises a suture, wherein the suture threaded through the perforations is used to attach the lead to a patient.
10. A method for implanting an epicardial implantable defibrillator lead in a patient in need thereof, the method comprising the steps of:
    making a transxiphoid or subxiphoid incision in the patient;
    accessing the pericardium;
    securing the lead to the diaphragmatic surface of the pericardium;
    advancing the lead into the pericardium; and
    closing the incision.
11. The method of claim 10, the step of securing comprising:
    stitching the lead to the diaphragmatic surface of the pericardium.
12. The method of claim 10, the method further comprising the step of:
    forming a loop in the lead.
13. The method of claim 12, the step of forming comprising:
    tying or stitching together two portions of the lead.
14. The method of claim 13, wherein a single suture ties or stitches together the two portions of the lead and secures the lead to the diaphragmatic surface of the pericardium.
15. The method of claim 10, wherein the step of advancing comprises:
    positioning the lead in a region proximal to the apex of the heart, the AV groove, and the left and right borders of the heart.
16. The method of claim 10, wherein the step of advancing comprises:
    positioning the lead on the diaphragm in a region corresponding to the inferior surface of the heart in a generally horizontal plane.
17. The method of claim 10, further comprising the step of:
    implanting a pulse generator in the subclavicular area of the subject; and
    connecting the pulse generator to the lead.
18. The method of claim 17, wherein the pulse generator is implanted in the patient's left side.
19. The method of claim 17, wherein the pulse generator is implanted in the patient's right side.

* * * * *